United States Patent
Castro (10) Patent No.: US 11,596,445 B2
(45) Date of Patent: Mar. 7, 2023

(54) IMPLANT FOR BONE

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 518 days.

(21) Appl. No.: 16/648,518

(22) PCT Filed: Oct. 3, 2019

(86) PCT No.: PCT/US2019/054383
§ 371 (c)(1),
(2) Date: Mar. 18, 2020

(87) PCT Pub. No.: WO2020/171849
PCT Pub. Date: Aug. 27, 2020

(65) Prior Publication Data
US 2020/0281628 A1 Sep. 10, 2020

Related U.S. Application Data

(60) Provisional application No. 62/809,670, filed on Feb. 24, 2019.

(51) Int. Cl.
*A61B 17/70* (2006.01)
*A61B 17/16* (2006.01)

(52) U.S. Cl.
CPC .......... *A61B 17/70* (2013.01); *A61B 17/1671* (2013.01); *A61B 17/7047* (2013.01); *A61B 17/7074* (2013.01)

(58) Field of Classification Search
CPC . A61B 17/70; A61B 17/1671; A61B 17/7074; A61B 17/7076
See application file for complete search history.

(56) References Cited

U.S. PATENT DOCUMENTS

| | | |
|---|---|---|
| 3,887,186 A | 2/1975 | Matlock, Jr. |
| 4,244,689 A | 1/1981 | Ashman |
| 6,159,211 A | 12/2000 | Boriani et al. |
| 6,447,525 B2 | 9/2002 | Follmer et al. |
| 6,743,255 B2 | 5/2004 | Ferree |
| 6,746,484 B1 | 6/2004 | Liu et al. |
| 8,100,972 B1 | 1/2012 | Bruffey et al. |
| 9,636,232 B2 | 5/2017 | Neubardt |
| 9,707,100 B2 | 7/2017 | Duffield et al. |
| 9,814,483 B2 | 11/2017 | Vardi |
| 9,867,733 B2 | 1/2018 | Mohan et al. |
| 2004/0078079 A1 | 4/2004 | Foley |
| 2004/0133279 A1 | 7/2004 | Krueger et al. |
| 2005/0119753 A1 | 6/2005 | McGahan et al. |
| 2006/0271053 A1 | 11/2006 | Schlapfer et al. |
| 2009/0254125 A1 | 10/2009 | Predick |
| 2009/0265006 A1 | 10/2009 | Seiftert et al. |
| 2010/0331895 A1 | 12/2010 | Linke |

(Continued)

FOREIGN PATENT DOCUMENTS

WO WO2001085069 11/2001

*Primary Examiner* — Ellen C Hammond
(74) *Attorney, Agent, or Firm* — Business Patent Law, PLLC (57) ABSTRACT

The present invention is an implant for bone. The current implant is particularly useful in spinal surgical procedures.

18 Claims, 4 Drawing Sheets

(56) References Cited

U.S. PATENT DOCUMENTS

| | | |
|---|---|---|
| 2011/0098747 A1 | 4/2011 | Donner et al. |
| 2011/0264229 A1 | 10/2011 | Donner |
| 2012/0010659 A1 | 1/2012 | Angert et al. |
| 2012/0232599 A1 | 9/2012 | Schoenly et al. |
| 2013/0150906 A1 | 6/2013 | Kerboul et al. |
| 2014/0066991 A1 | 3/2014 | Marik et al. |
| 2014/0200618 A1* | 7/2014 | Donner .................. A61F 2/4611 606/281 |
| 2016/0184099 A1 | 6/2016 | Gotfried |
| 2016/0310294 A1 | 10/2016 | McConnell et al. |

* cited by examiner

IMPLANT FOR BONE

PRIORITY

Applicant claims priority to PCT/US2019/054383—Implant for Bone—, Filed Oct. 3, 2019 that claims the benefit of U.S. Provisional Application No. 62/809,670—Implant for Bone—filed on Feb. 24, 2019.

BACKGROUND OF THE INVENTION

A. Field of the Invention

Among other things, the present invention is an implant for bone. The current implant is particularly suited for implantation into mammalian spinal tissues. The present implant is provided with a cutting blade. Select embodiments of the current invention include surface treatments in anticipation of improving attachment of bone to the implant.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art for the current invention include: 1) US Published Patent Application 20040133279-Krueger, et al. discloses surgical implants for use as spinal spacers; 2) US Published Patent Application 20050119753-McGahan, et al. discloses anterior impacted bone graft and driver instruments; 3) World Intellectual Property Organization Published Patent Application No. WO2001085069-Scient'X discloses an anterior lumbar interbody implant; 4) US Published Patent Application 20160310294-McConnell, et al. discloses a spinal fusion implant for oblique insertion; 5) U.S. Pat. No. 6,159,211-Boriani, et al. a stackable cage system for corpectomy/vertebrectomy; 6) U.S. Pat. No. 6,743,255-Ferree discloses a spinal fusion cage with lordosis correction; and 7) U.S. Pat. No. 6,746,484-Liu, et al. discloses a spinal implant.

SUMMARY OF THE INVENTION

The present invention provides a biocompatible implant for bone that can be interlocked with a device distinct from the implant. The current implant is also provided with a blade for cutting tissue. Preferred embodiments of the current fastener can also be utilized for transporting biocompatible devices/substances, such as adhesives, cameras, cannulas, fiber optics, implants, pharmaceuticals, etc. Preferred embodiments of the implant's blade are provided with an aperture. The aperture can assist tissue growth, such as bone, into and through the implant as well onto the inward surfaces of the implant. Select embodiments of the implant are provided with surface treatments in anticipation of improving attachment of bone to the implant.

With regard to spinal surgical procedures, prior art traditional fixation screws fixation stability is dependent on the healthy composition of the cancellous bone. Those skilled in the art recognize the healthy cortical bone is from about 20 to about 100 times stronger than healthy cancelleous bone. Those skilled in the art also know that increasing the screw length for osteoporotic bone rarely provides satisfactory resistance against the fixation screw from pulling-out or backing-out of bone. The blade of the current implant is shorter and wider than traditional fixation screws. Because of its novel structure and surgical insertion technique, the present implant has greater resistance against pulling-out or backing-out of osteoporotic bone. Further still, the blade's shorter length reduces the possibility of injury to nearby structures such as arteries, veins and nervous tissues. It is believed that the current invention's resistance to pull-out or back-out improves implant-construct stability, higher bone fusion rates and better postoperative clinical outcomes than prior art fixation screws.

For surgical procedures involving bone, the current implant can be inserted through a small linear aperture into the bone tissue. In one of the preferred uses of the current implant, subsequent to blade's surgical insertion into bone, the blade can be rotated up to 90 degrees relative to the plane of the surgical incision. Among other things, rotation of the blade increases resistance against pull-out or back-out of the blade from bone when compared to prior art fixation screws. It is also believed that the width of the implant's blade can contact a greater surface area of healthier cortical bone distinct from the surgically created cavity, thereby improving the possibility of successful postoperative bone fusion relative to prior art fixation screws.

Within the scope of the current invention, blades can be of symmetrical or asymmetrical configuration.

Symmetrical blades are typically preferred when the inner cortex is straight—a straight inner cortex as viewed from a lateral X-ray perspective looking at the spine. Asymmetrical blades are generally preferred when the inner cortex is sloped as seen on a lateral X-ray or sagittal CT scan). Regardless of whether symmetrical or asymmetrical, implants within the scope of the current invention require insertion and subsequent rotation of the blade of up to 90 degrees relative to the plane of the surgical incision.

In use, any surgical connecting rods will generally be parallel to the blades. In a first example for a laminectomy and fusion procedure, connecting rods and the present implant's blades will be generally vertical. In a second example for a laminoplasty procedure, the connecting rods and current implant's blades will be horizontal extending from the right side of the spinal elements to the left side spinal elements. The surgical incision will be up to 90 degrees offset from the final orientation of the implant's blade.

Various asymmetrical blade configurations are typically preferred when the surgical insertion corridor is not cylindrical. By way of illustration, when the current device is implanted into the posterior cervical facets, the blade is initially inserted through the posterior cortex perpendicular to the axis of the spinal cord. After insertion, the blade is rotated up to 90 degrees to be parallel to the axis of the spinal cord. It is believed that the asymmetrical blade allows for a greater surface area contact of the posterior cortex.

An aspect of the present invention is to provide an implant with a cutting blade.

Still another aspect of the present invention is to provide an implant with a blade that can be rotated up to 90 degrees relative to the surgical incision.

It is still another aspect of the present invention to provide an implant that improves resistance to pull-out or back-out and improves implant-construct stability, higher bone fusion rates and better postoperative clinical outcomes than prior art fixation screws.

Yet still another aspect of the present invention is to provide an implant with greater resistance against pulling-out or backing-out of osteoporotic bone that current fixation screws.

Still another aspect of the present invention is to provide an implant adapted for connection with a device distinct from the implant.

Yet another aspect of the present invention is to provide an implant with a conduit for transporting biocompatible devices/substances or chemotherapeutic agents.

It is still another aspect of the present invention to provide an implant with a blade having an aperture therein.

Yet still another aspect of the present invention is to provide an implant adaptable for use in the cervical region of the spine.

A preferred embodiment of the current invention can be described as a spinal implant adapted for interconnection with a device distinct from the spinal implant; the spinal implant comprising: a) a cylindrical shaft comprising a first end, a second end opposite the first end and an inner cavity extending from the first end to the second end; b) the first end of the cylindrical shaft further comprising a helical external thread running from the first end toward the second end for a predetermined distance less than the length of the cylindrical shaft, wherein the thread is adapted for connecting with the device distinct from the spinal implant; and c) a surgical blade comprising: i) an arcuate side wider than a diameter of the second end of the cylindrical shaft and connected to the second end of the cylindrical shaft, wherein the arcuate side comprises first and second opposed wings; ii) a straight side opposite the arcuate first side; the straight side of a lesser length than the arcuate side; iii) first and second converging edges connected with the arcuate side and converging toward each other as the first and second converging edges approach the straight side; and iv) an aperture proximate the center of the surgical blade.

Another preferred embodiment of the current invention can be described as a spinal implant adapted for interconnection with a device distinct from the spinal implant; the spinal implant comprising: a) a cylindrical shaft comprising a first end, a second end opposite the first end and an inner cavity extending from the first end to the second end; b) the first end of the cylindrical shaft further comprising a polyaxial head mounted to the first end, wherein the polyaxial head is adapted for connection with the device distinct from the spinal implant; and c) a surgical blade comprising: i) an arcuate side wider than a diameter of the second end of the cylindrical shaft and connected to the second end of the cylindrical shaft, wherein the arcuate side comprises first and second opposed wings; ii) a straight side opposite the arcuate side; the straight side of a lesser length than the arcuate side; iii) first and second converging edges connected with the arcuate side and converging toward each other as the first and second converging edges approach the straight side; and iv) an aperture proximate the center of the surgical blade.

Still another preferred embodiment of the current invention can be described as a spinal implant adapted for interconnection with a device distinct from the spinal implant; the spinal implant comprising: a) a cylindrical shaft comprising a first end, a second end opposite the first end and an inner cavity extending from the first end to the second end; b) the first end of the cylindrical shaft further comprising a polyaxial head mounted to the first end, wherein the polyaxial head is adapted for connection with the device distinct from the spinal implant; and c) a surgical blade comprising: i) a slanted side relative to and wider than a diameter of the second end of the cylindrical shaft and connected to the second end of the cylindrical shaft, wherein the slanted side comprises a first wing positioned on a first side of the cylindrical shaft and a second wing positioned on a second side of the cylindrical shaft; ii) a straight side opposite the slanted side; the straight side of a lesser length than the slanted side; iii) first and second converging edges connected with the slanted side and converging toward each other as the first and second converging edges approach the straight side; and iv) an aperture proximate the center of the surgical blade.

Yet another preferred embodiment of the current invention can be described as a spinal implant adapted for interconnection with a device distinct from the spinal implant; the spinal implant comprising: a) a cylindrical shaft comprising a first end, a second end opposite the first end and an inner cavity extending from the first end to the second end; b) the first end of the cylindrical shaft further comprising a helical external thread running from the first end toward the second end for a predetermined distance less than the length of the cylindrical shaft, wherein the thread is adapted for connecting with the device distinct from the spinal implant; and c) a surgical blade comprising: i) a slanted side relative to and wider than a diameter of the second end of the cylindrical shaft and connected to the second end of the cylindrical shaft, wherein the slanted side comprises a first wing positioned on a first side of the cylindrical shaft and a second wing positioned on a second side of the cylindrical shaft; ii) a straight side opposite the slanted side; the straight side of a lesser length than the slanted side; iii) first and second converging edges connected with the slanted side and converging toward each other as the first and second converging edges approach the straight side; and iv) an aperture proximate the center of the surgical blade.

Another preferred embodiment of the current invention can be described as a spinal implant (30) adapted for interconnection with a device distinct from the spinal implant; the spinal implant comprising: a) a cylindrical shaft comprising a first end, a second end opposite the first end and an inner cavity extending from the first end to the second end; and b) a surgical blade comprising: i) an arcuate side wider than a diameter of the second end of the cylindrical shaft and connected to the second end of the cylindrical shaft, wherein the arcuate side comprises first and second opposed wings; ii) a straight side opposite the arcuate side; the straight side of a lesser length than the arcuate side; iii) first and second converging edges connected with the arcuate side and converging toward each other as the first and second converging edges approach the straight side; and iv) an aperture proximate the center of the surgical blade.

Still another preferred embodiment of the current invention can be described as a spinal implant adapted for interconnection with a device distinct from the spinal implant (30); the spinal implant comprising: a) a cylindrical shaft comprising a first end, a second end opposite the first end and an inner cavity extending from the first end to the second end; and b) a surgical blade comprising: i) a slanted side relative to and wider than a diameter of the second end of the cylindrical shaft and connected to the second end of the cylindrical shaft, wherein the slanted side comprises a first wing positioned on a first side of the cylindrical shaft and a second wing positioned on a second side of the cylindrical shaft; ii) a straight side opposite the slanted side; the straight side of a lesser length than the slanted side; iii) first and second converging edges connected with the slanted side and converging toward each other as the first and second converging edges approach the straight side; and iv) an aperture proximate the center of the surgical blade.

It is the novel and unique interaction of these simple elements which creates the apparatus and methods, within the ambit of the present invention. Descriptions of preferred embodiments of the invention follow. However, it is to be understood that the best mode descriptions do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

In the most general sense, the present invention is an implant for bone where the implant is adapted for connection with a device distinct from the implant. Among other things, the current invention can be adapted for use with vertebra or other bone tissues. The present implant is particularly adapted for use in the cervical region of the spine. The current invention can be provided with a conduit for transporting biocompatible devices/substances or chemotherapeutic agents, such as adhesives, cameras, cannulas, fiber optics, implants, pharmaceuticals, etc. Dispersion of adhesives from the windows or openings of the implant before closing the surgical wound, reduces the risk of the fastener backing out of the wound prior to the fastener fully interlocking with tissue overgrowth. Polymethymethacrylate is an adhesive particularly well suited for use with the current fastener.

Preferred embodiments of the present invention are manufactured of titanium alloys, stainless steel, non-resorbable polymers or any other composition acceptable in the art. Within the scope of the present invention, it has advantageously been discovered that cylindrical shafts (40) can have lengths from about 2 to about 10 millimeters; polyaxial heads (50) can have lengths of from about 5 millimeters to about 25 millimeters; sockets (54) of polyaxial heads (50) can have depths from about 3 millimeters to about 23 millimeters, diameters from about 4 millimeters to about 20 millimeters, lateral openings widths (62, 64) from about 3 millimeters to about 10 millimeters; and blades (80, 120) can have lengths of from about 3 millimeters to about 12 millimeters, widths of from about 4 millimeters to about 10 millimeters and heights of from about 0.2 millimeters to about 4 millimeters.

Figure 1:
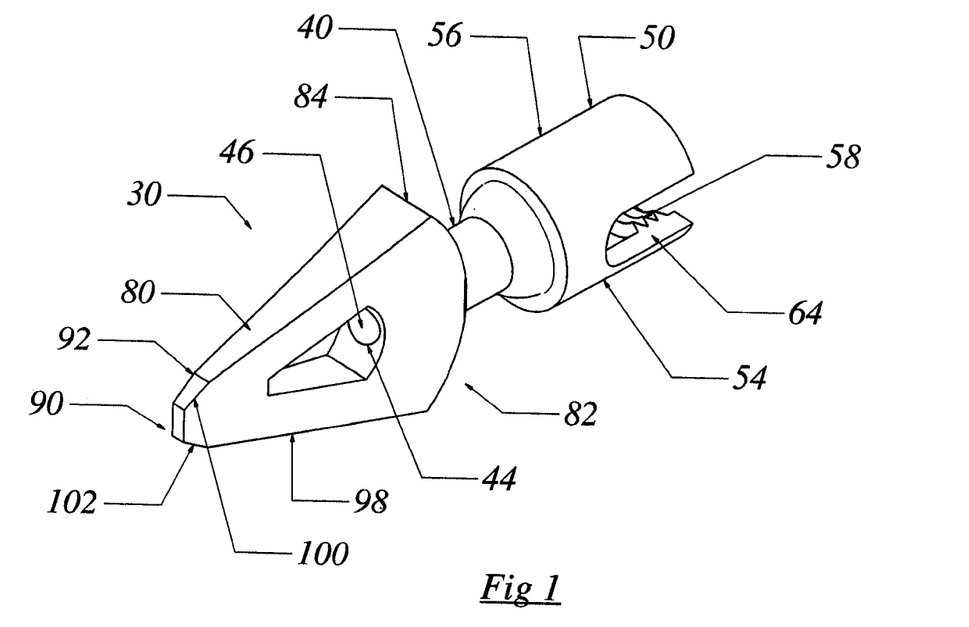
FIG. 1 is a perspective of a first preferred embodiment of the implant.
Figure 2:
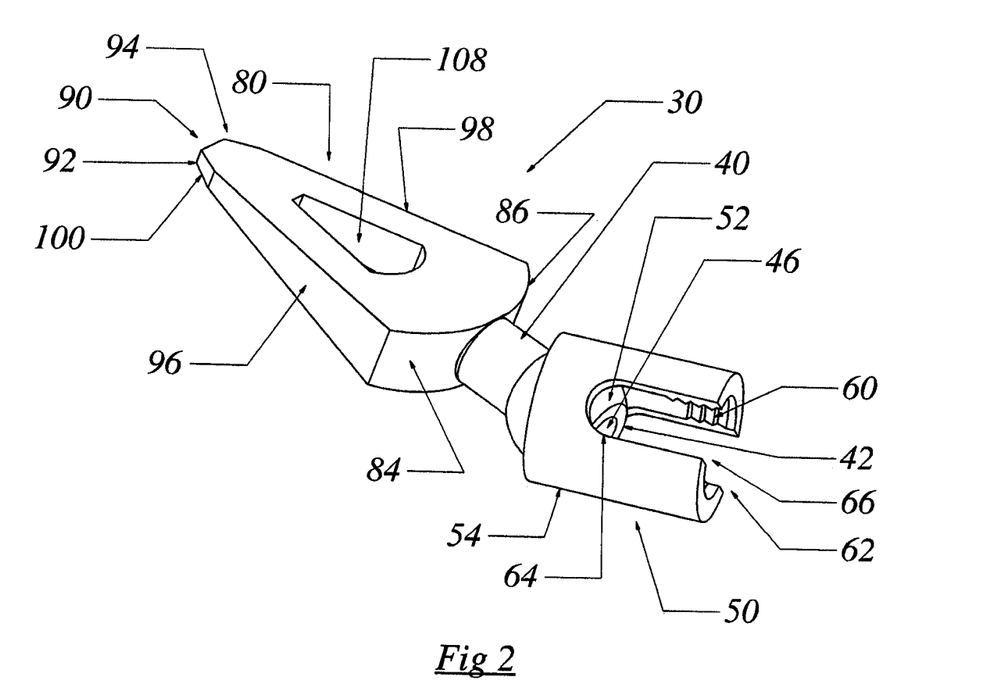
FIG. 2 is a perspective of a first preferred embodiment of the implant.

FIGS. 1 and 2 are perspectives of a first preferred embodiment of implant (30). Within the scope of the current invention, implant (30) can be interconnected with a device distinct from the implant. It has been discovered that implant (30) is useful for spinal surgeries, and, in particular, surgeries for the cervical region of the spine.

Among other things, the preferred embodiment of implant (30), enabled in FIGS. 1 and 2, includes cylindrical shaft (40), polyaxial head (50) and blade (80). Cylindrical shaft (40) includes first end (42), second end (44) and inner cavity (46) extending through first end (42) and second end (44).

Polyaxial head (50) of implant (30) is adapted for connection with a device (not shown) distinct from implant (30). Examples of devices connectable to polyaxial head (40) include but are not limited to: rods, bars, cross-links, screws and locking nuts. Polyaxial head (50) is provided with spheroid (52) connected to first end (42) of cylindrical shaft (40) and socket (54) connected to spheroid (52). Prior to surgical fixation, the combination of spheroid (52) and socket (54) allows polyaxial head (50) to be moved in a multitude of axes relative to the inner cavity (46) of cylindrical shaft (40). Socket (54) is provided with an outward housing (56) and inward receptacle (58) including one or more threads (60). Selected preferred embodiments of housing (56) can be provided with openings (62, 64, 66) adapted to receive one or more devices distinct from implant (30).

Arcuate side (82) of blade (80) is connected with second side (44) of cylindrical shaft (40). Arcuate side (82) of blade (80) is of a dimension wider than the diameter of cylindrical shaft (40). Arcuate side (82) includes first wing (84) and second wing (86) where each wing (84, 86) extends away from the longitudinal axis of cylindrical shaft (40). As shown in FIGS. 1 and 2, each wing (84, 86) is arched away from first end (42) of cylindrical shaft (40).

Straight side (90) of blade (80) is of lesser length than arcuate side (82) and positioned opposite from arcuate side (82). Straight side (90) includes first end (92) and second end (94). First converging edge (96) connected to first wing (84) and second converging edge (98) connected second wing (86) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial, osteogenic or chemotherapeutic substances into the surgically created cavity.

Figure 3:
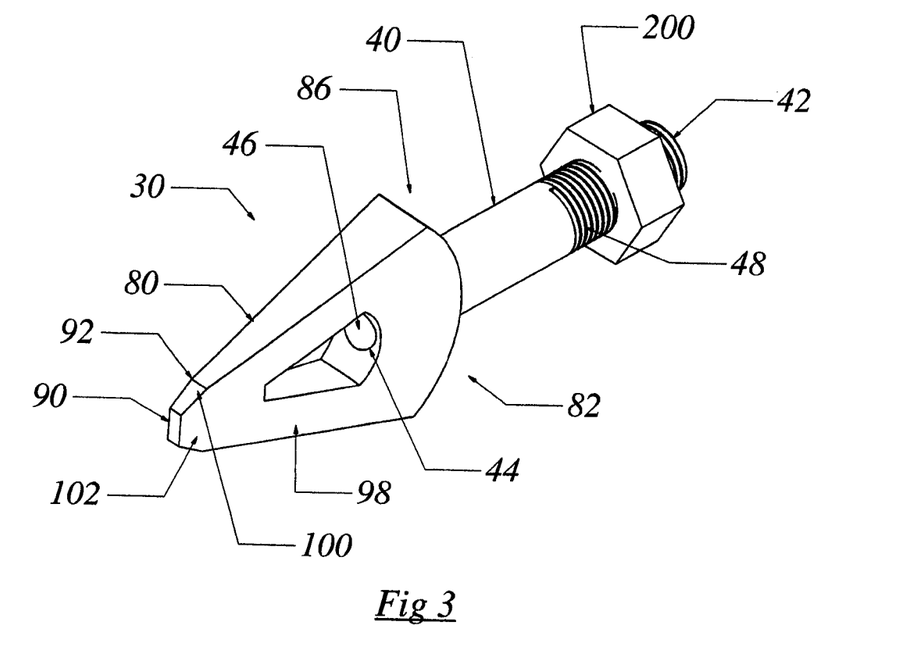
FIG. 3 is a perspective of a second preferred embodiment of the implant.
Figure 4:
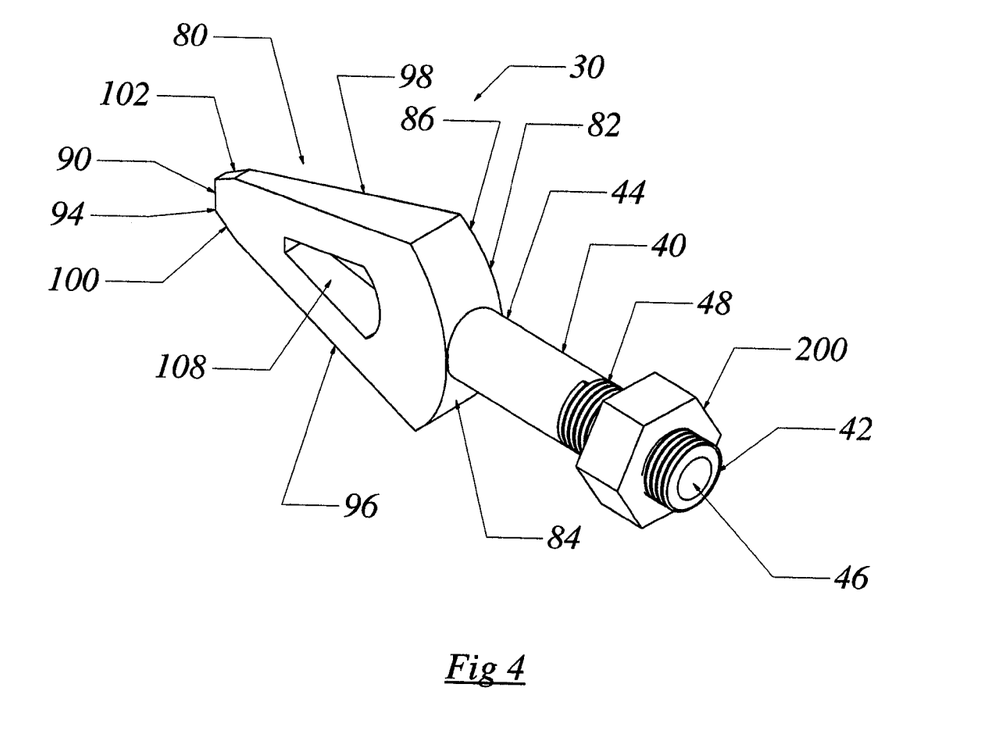
FIG. 4 is a perspective of a second preferred embodiment of the implant.

FIGS. 3 and 4 are perspectives of a second preferred embodiment of implant (30). Within the scope of the current invention, implant (30) can be interconnected with a device distinct from the implant, such as a nut (200) or other device (not shown) for coupling with implant (30). It has been discovered that implant (30) is useful for spinal surgeries, and, in particular, surgeries for the cervical region of the spine.

Among other things, the preferred embodiment of implant (30), enabled in FIGS. 3 and 4, includes cylindrical shaft (40) and blade (80). Cylindrical shaft (40) includes first end (42), second end (44) and inner cavity (46) extending through first end (42) and second end (44). First end (42) of cylindrical shaft (40) is provided with thread (48) that can be utilized to connect implant (30) to a device distinct from implant (30). Thread (48) runs about at least a portion of the outward side of cylindrical shaft (40) and advances from first end (42) toward the second end (44) of cylindrical shaft (40).

Arcuate side (82) of blade (80) is connected with second side (44) of cylindrical shaft (40). Arcuate side (82) of blade (80) is of a dimension wider than the diameter of cylindrical shaft (40). Arcuate side (82) is also provided with first wing (84) and second wing (86) where each wing (84, 86) extends away from the longitudinal axis of cylindrical shaft (40). As shown in FIGS. 1 and 2, each wing (84, 86) is arched away from first end (42) of cylindrical shaft (40).

Straight side (90) of blade (80) is of lesser length than arcuate side (82) and positioned opposite from arcuate side (82). Straight side (90) includes first end (92) and second end (94). First converging edge (96) connected to first wing (84) and second converging edge (98) connected second wing (86) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Figure 5:
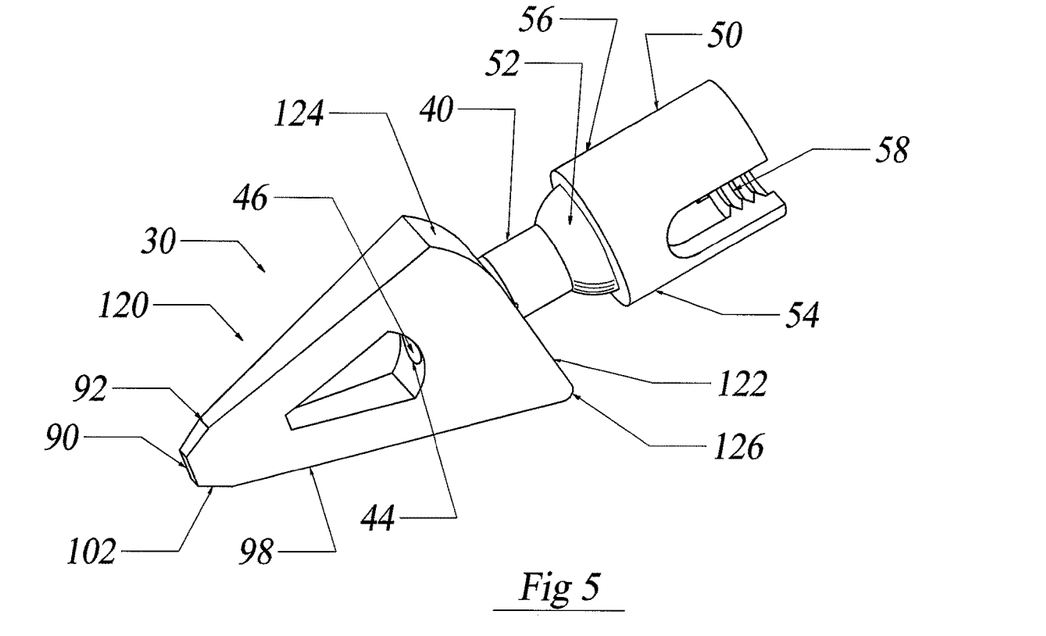
FIG. 5 is a perspective of a third preferred embodiment of the implant.
Figure 6:
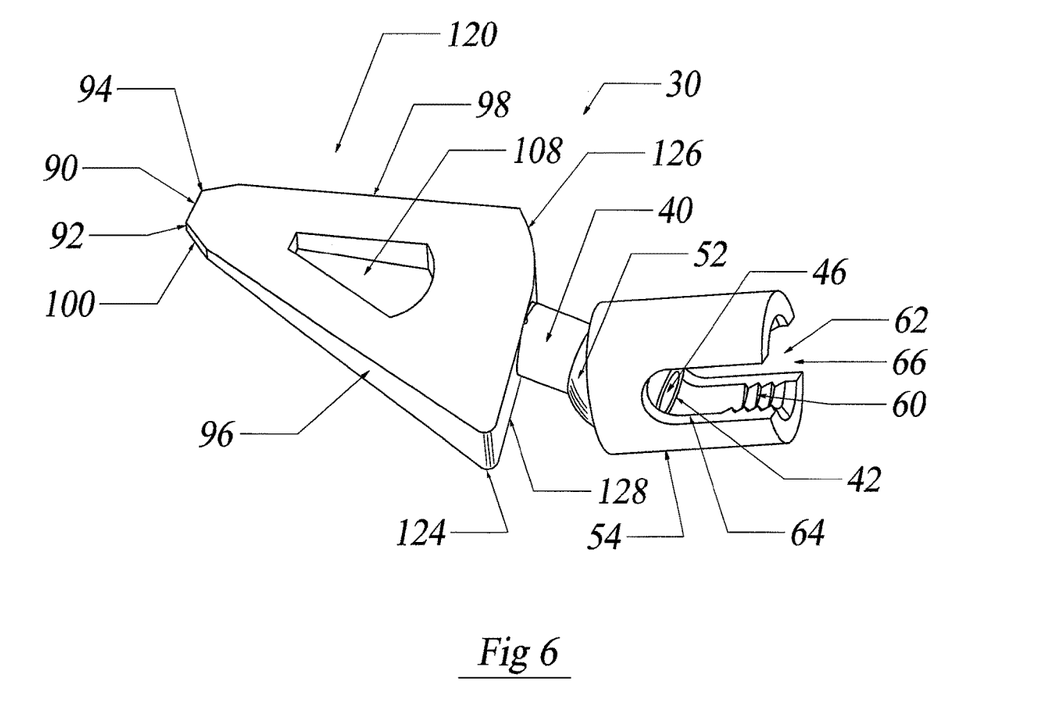
FIG. 6 is a perspective of a third preferred embodiment of the implant.

FIGS. 5 and 6 are perspectives of a third preferred embodiment of implant (30). Within the scope of the current invention, implant (30) can be interconnected with a device distinct from the implant. It has been discovered that implant (30) is useful for spinal surgeries, and, in particular, surgeries for the cervical region of the spine.

Among other things, the preferred embodiment of implant (30), enabled in FIGS. 5 and 6, includes cylindrical shaft (40), polyaxial head (50) and blade (120). Cylindrical shaft (40) includes first end (42), second end (44) and inner cavity (46) extending through first end (42) and second end (44).

Polyaxial head (50) of implant (30) is adapted for connection with a device (not shown) distinct from implant (30). Examples of devices connectable to polyaxial head (50) include but are not limited to: rods, cross-links, bars, screws, and locking nuts. Polyaxial head (50) is provided with spheroid (52) connected to first end (42) of cylindrical shaft (40) and socket (54) connected to spheroid (52). Prior to surgical fixation, the combination of spheroid (52) and socket (54) allows polyaxial head (50) to be moved in a multitude of axes relative to the longitudinal axis or inner cavity (46) of cylindrical shaft (40). Socket (54) is provided with an outward housing (56) and inward receptacle (58) including one or more threads (60). Selected preferred embodiments of housing (56) can be provided with openings (62, 64, 66) adapted to receive one or more devices distinct from implant (30).

Slanted side (122) of blade (120) is connected with second side (44) of cylindrical shaft (40). Slanted side (122) of blade (120) is of a dimension wider than the diameter of cylindrical shaft (40). Slanted side (122) includes first wing (124) and second wing (126) where each wing (124, 126) extends away from the longitudinal axis of cylindrical shaft (40). As shown in FIGS. 5 and 6, a first one of the wings (124, 126) is arcuate and arched away from the first end cylindrical shaft (40). A second one of the wings (124, 126) is provided with a pitched plane (128) facing first end (42) of cylindrical shaft (40). The combination of an arcuate wing and a wing including a pitched plane creates an asymmetric blade (120). Pitched plane (128) intersects the longitudinal axis of implant (30) at an angle of between five and eighty five degrees as measured from the distal point of pitched plane (128) to the intersection of pitched plane and implant's (30) longitudinal axis.

Straight side (90) of blade (120) is of lesser length than slanted side (122) and positioned opposite from slanted side (122). Straight side (90) includes first end (92) and second end (94). First converging edge (96) connected to first wing (124) and second converging edge (98) connected second wing (126) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Figure 7:
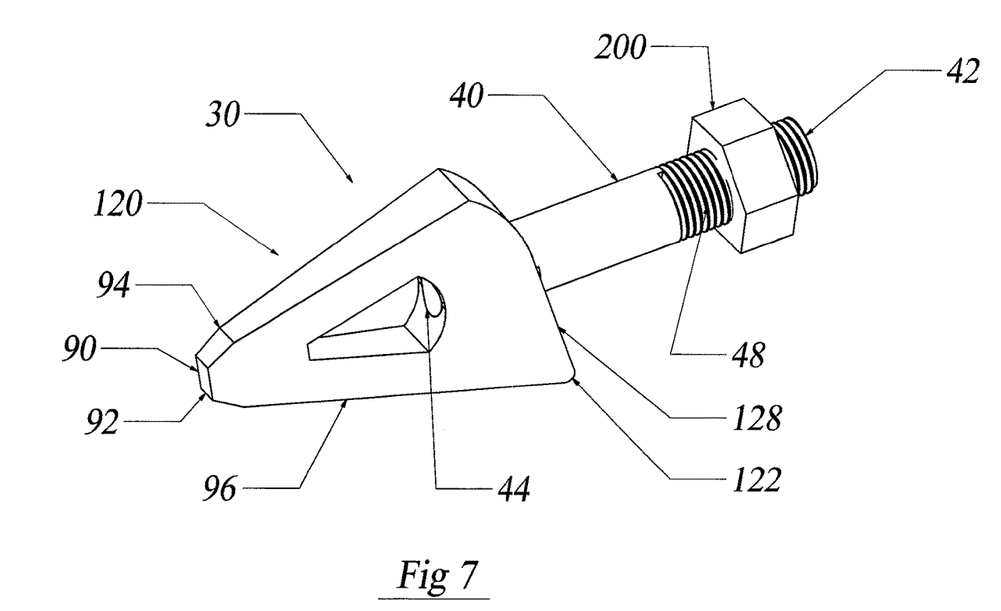
FIG. 7 is a perspective of a fourth preferred embodiment of the implant.
Figure 8:
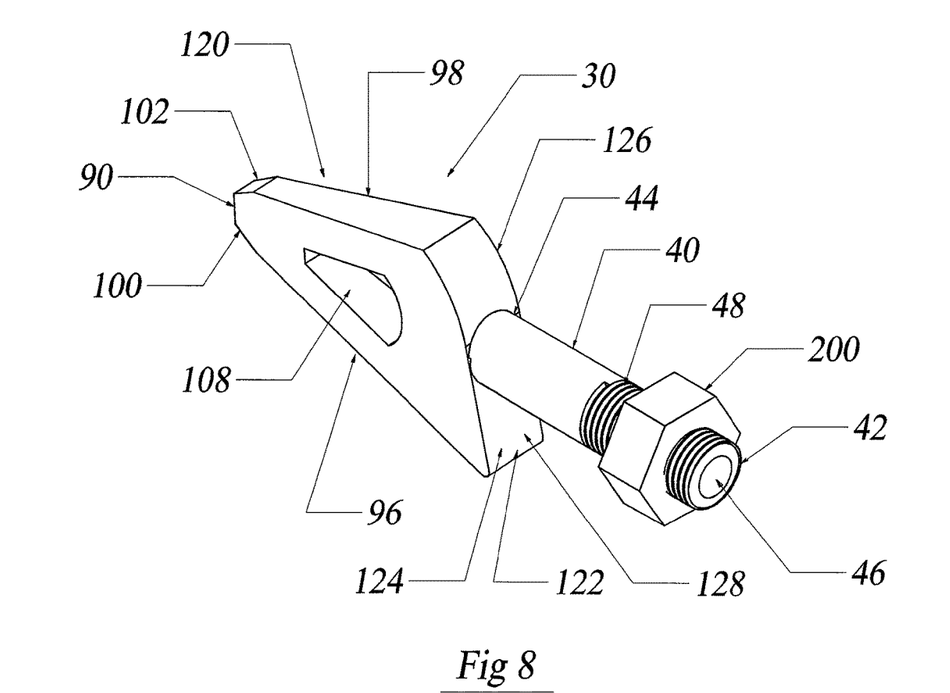
FIG. 8 is a perspective of a fourth preferred embodiment of the implant.

FIGS. 7 and 8 are perspectives of a fourth preferred embodiment of implant (30). Within the scope of the current invention, implant (30) can be interconnected with a device distinct from the implant, such as a nut (200) or other device (not shown) for coupling with implant (30). It has been discovered that implant (30) is useful for spinal surgeries, and, in particular, surgeries for the cervical region of the spine.

Among other things, the preferred embodiment of implant (30), enabled in FIGS. 7 and 8, includes cylindrical shaft (40) and blade (120). Cylindrical shaft (40) includes first end (42), second end (44) and inner cavity (46) extending through first end (42) and second end (44). First end (42) of cylindrical shaft (40) is provided with thread (48) that can be utilized to connect implant (30) to a device distinct from implant (30). Thread (48) runs about at least a portion of the outward side of cylindrical shaft (40) and advances from first end (42) toward the second end (44) of cylindrical shaft (40).

Slanted side (122) of blade (120) is connected with second side (44) of cylindrical shaft (40). Slanted side (122) of blade (120) is of a dimension wider than the diameter of cylindrical shaft (40). Slanted side (122) includes first wing (124) and second wing (126) where each wing (124, 126) extends away from the longitudinal axis of cylindrical shaft (40). As shown in FIGS. 7 and 8, a first one of the wings (124, 126) is arcuate and arched away from the first end cylindrical shaft (40). A second one of the wings (124, 126) is provided with a pitched plane (128) facing first end (42) of cylindrical shaft (40). The combination of an arcuate wing and a wing including a pitched plane creates an asymmetric blade (120). Pitched plane (128) intersects the longitudinal axis of implant (30) at an angle of between five and eighty five degrees as measured from the distal point of pitched plane (128) to the intersection of pitched plane and implant's (30) longitudinal axis.

Straight side (90) of blade (120) is of lesser length than slanted side (122) and positioned opposite from slanted side (122). Straight side (90) includes first end (92) and second end (94). First converging edge (96) connected to first wing (124) and second converging edge (98) connected second wing (126) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Applicant has enabled, described and disclosed the invention as required by the Patent Cooperation Treaty and Title 35 of the United States Code.

What is claimed is:

1. A spinal implant adapted for interconnection with a device distinct from the spinal implant; the spinal implant comprising:
   a) a cylindrical shaft comprising a first end, a second end opposite the first end and an inner cavity extending from the first end to the second end;
   b) the first end of the cylindrical shaft further comprising a polyaxial head mounted to the first end, wherein the polyaxial head is adapted for connection with the device distinct from the spinal implant; and
   c) a surgical blade comprising:
      i) an arcuate side wider than a diameter of the second end of the cylindrical shaft and connected to the second end of the cylindrical shaft, wherein the arcuate side comprises first and second opposed wings;
      ii) a straight side opposite the arcuate side; the straight side of a lesser length than the arcuate side;
      iii) first and second converging edges connected with the arcuate side and converging toward each other as the first and second converging edges approach the straight side; and
      iv) an aperture proximate the center of the surgical blade; the aperture, positioned between the first and second converging edges, opening to opposed sides of a surgically created space.

2. The spinal implant of claim 1, wherein the polyaxial head comprises an outer housing and a threaded inward receptacle adapted to receive the device distinct from the spinal implant.

3. The spinal implant of claim 2 comprising a first transition edge connected to the first converging edge and the straight side and a second transition edge connected to the second converging edge and the straight side.

4. The spinal implant of claim 3, wherein the first wing and the second wing are arched away from the first end of the cylindrical shaft and the inner cavity creates a junction with the aperture.

5. A spinal implant adapted for interconnection with a device distinct from the spinal implant; the spinal implant comprising:
   a) a cylindrical shaft comprising a first end, a second end opposite the first end and an inner cavity extending from the first end to the second end;
   b) the first end of the cylindrical shaft further comprising a polyaxial head mounted to the first end, wherein the polyaxial head is adapted for connection with the device distinct from the spinal implant; and
   c) a surgical blade comprising:
      i) a slanted side relative to and wider than a diameter of the second end of the cylindrical shaft and connected to the second end of the cylindrical shaft, wherein the slanted side comprises a first wing positioned on a first side of the cylindrical shaft and a second wing positioned on a second side of the cylindrical shaft;
      ii) a straight side opposite the slanted side; the straight side of a lesser length than the slanted side;
      iii) first and second converging edges connected with the slanted side and converging toward each other as the first and second converging edges approach the straight side; and
      iv) an aperture proximate the center of the surgical blade; the aperture, positioned between the first and second converging edges, opening to opposed sides of a surgically created space.

6. The spinal implant of claim 5, wherein the polyaxial head comprises an outer housing and a threaded inward receptacle adapted to receive the device distinct from the spinal implant.

7. The spinal implant of claim 6 comprising a first transition edge connected to the first converging edge and the straight side and a second transition edge connected to the second converging edge and the straight side.

8. The spinal implant of claim 7, wherein the slanted side intersects with the longitudinal axis of cylindrical shaft at angles other than perpendicular.

9. The spinal implant of claim 8, wherein either the first wing or the second wing is arcuate and the inner cavity creates a junction with the aperture.

10. A spinal implant adapted for interconnection with a device distinct from the spinal implant; the spinal implant comprising:

a) a cylindrical shaft comprising a first end, a second end opposite the first end and an inner cavity extending from the first end to the second end; and b) a surgical blade comprising:
  i) an arcuate side wider than a diameter of the second end of the cylindrical shaft and connected to the second end of the cylindrical shaft, wherein the arcuate side comprises first and second opposed wings;
  ii) a straight side opposite the arcuate side; the straight side of a lesser length than the arcuate side, and wherein the longitudinal axis of the cylindrical shaft extends through the straight side;
  iii) first and second converging edges connected with the arcuate side and converging toward each other as the first and second converging edges approach the straight side; and
  iv) an aperture proximate the center of the surgical blade; the aperture, positioned between the first and second converging edges, opening to opposed sides of a surgically created space.

11. The spinal implant of claim 10 comprising a first transition edge connected to the first converging edge and the straight side and a second transition edge connected to the second converging edge and the straight side.

12. The spinal implant of claim 11, wherein the first wing and the second wing are arched away from the first end of the cylindrical shaft and the inner cavity creates a junction with the aperture.

13. The spinal implant of claim 12, wherein the first end of the cylindrical shaft comprises a polyaxial head mounted to the first end; the polyaxial head adapted for connection with the device distinct from the spinal implant.

14. A spinal implant adapted for interconnection with a device distinct from the spinal implant; the spinal implant comprising:

a) a cylindrical shaft comprising a first end, a second end opposite the first end and an inner cavity extending from the first end to the second end; and b) a surgical blade comprising:
  i) a slanted side relative to and wider than a diameter of the second end of the cylindrical shaft and connected to the second end of the cylindrical shaft, wherein the slanted side comprises a first wing positioned on a first side of the cylindrical shaft and a second wing positioned on a second side of the cylindrical shaft;
  ii) a straight side opposite the slanted side; the straight side of a lesser length than the slanted side, and wherein the longitudinal axis of the cylindrical shaft extends through the straight side;
  iii) first and second converging edges connected with the slanted side and converging toward each other as the first and second converging edges approach the straight side; and
  iv) an aperture proximate the center of the surgical blade; the aperture, positioned between the first and second converging edges, opening to opposed sides of a surgically created space.

15. The spinal implant of claim 14 comprising a first transition edge connected to the first converging edge and the straight side and a second transition edge connected to the second converging edge and the straight side.

16. The spinal implant of claim 15, wherein the slanted side intersects with the longitudinal axis of cylindrical shaft at angles other than perpendicular.

17. The spinal implant of claim 16, wherein either the first wing or the second wing is arcuate and the inner cavity creates a junction with the aperture.

18. The spinal implant of claim 17, wherein the first end of the cylindrical shaft comprises a polyaxial head mounted to the first end; the polyaxial head adapted for connection with the device distinct from the spinal implant.

* * * * *